United States Patent
Bernhardt et al.

(10) Patent No.: US 7,298,882 B2
(45) Date of Patent: Nov. 20, 2007

(54) GENERALIZED MEASURE OF IMAGE QUALITY IN MEDICAL X-RAY IMAGING

(75) Inventors: Philipp Bernhardt, Forchheim (DE); Lothar Bätz, Heroldsberg (DE); Ernst-Peter Rührnschopf, Erlangen (DE); Martin Hoheisel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 219 days.

(21) Appl. No.: 11/058,025

(22) Filed: Feb. 15, 2005

(65) Prior Publication Data

US 2006/0182322 A1    Aug. 17, 2006

(51) Int. Cl.
*G06T 5/00* (2006.01)

(52) U.S. Cl. .................. 382/128; 382/264; 382/280

(58) Field of Classification Search ............... None
See application file for complete search history.

(56) References Cited

U.S. PATENT DOCUMENTS 5,396,531 A * 3/1995 Hartley .................. 378/108
5,440,647 A * 8/1995 Floyd et al. ............. 382/132
5,671,263 A * 9/1997 Ching-Ming .............. 378/8
5,886,359 A * 3/1999 Bringley et al. .......... 250/580

OTHER PUBLICATIONS

Med. Phys. 30(11), Nov. 2003; Robert S. Saunders, Jr., et al., 3006-3017.*
Med. Phys. 21(3), Mar. 1994; I. A. Cunningham et al.; 417-427.*
Med. Phys. 31(10), Oct. 2004; E. Guibelalde et al.; 2819-2825.*
IEEE Sep. 1995; I. A. Cunningham et al.; 555-556.*
Medical Imaging (SPIE vol. 5368) 2004; M. Hoheisel et al.; 386-395□□.*

* cited by examiner

*Primary Examiner*—Brian P. Werner
*Assistant Examiner*—Eueng-nan Yeh
(74) *Attorney, Agent, or Firm*—Schiff Hardin LLP

(57) ABSTRACT

A method for defining image quality characteristics of X-ray based medical projection imaging devices is provided. A spatial frequency-dependent signal-to-noise ratio function includes image quality parameters of spatial resolution, object contrast and noise. The detectability of an object embedded into a defined background, such as a cardiac guide wire in a patient is determined. An X-ray system may be defined and set up for obtaining an optimized image quality to determine the best object detectability for a given patient dose.

11 Claims, 5 Drawing Sheets

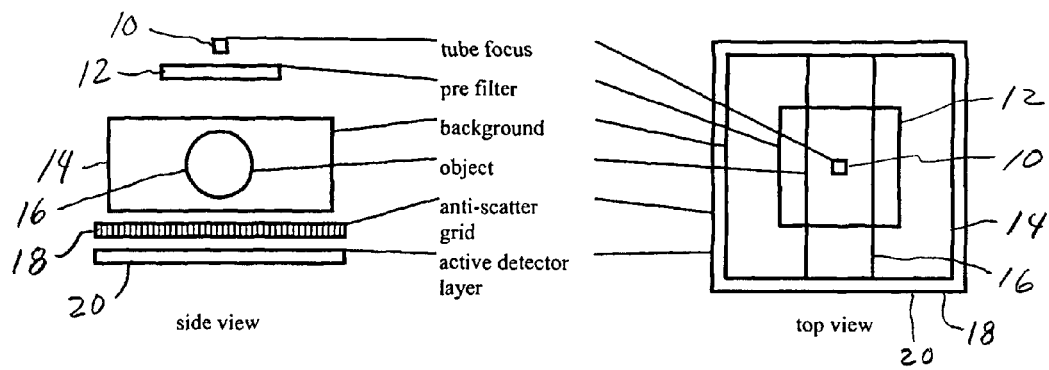
Fig. 1A
Fig. 1B
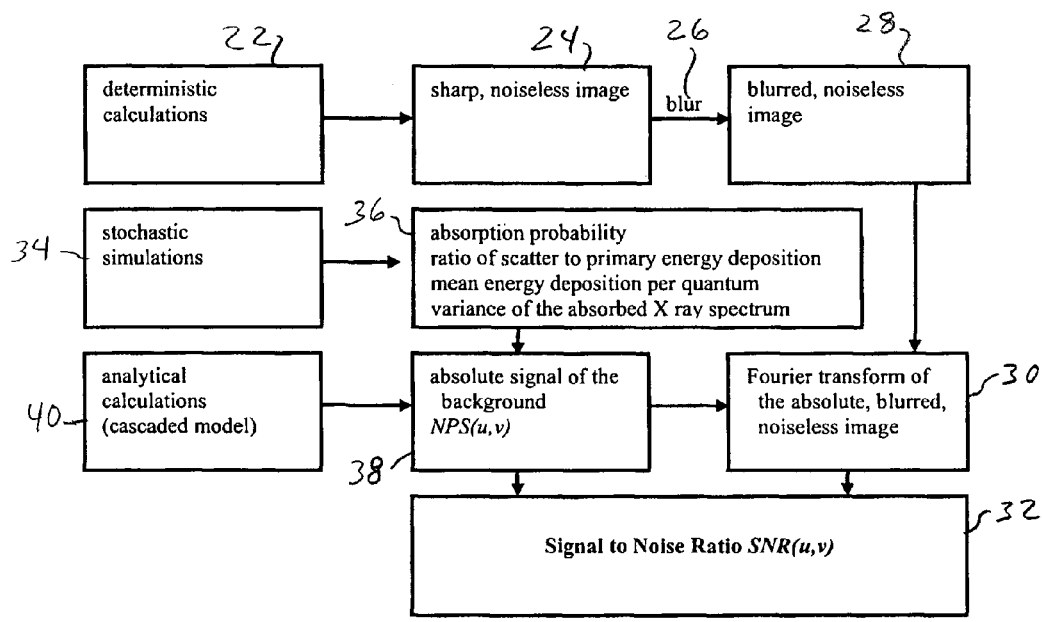
Fig. 2

0.5 ms 4.5 ms 6.3 ms 9.0 ms 13.5 ms 18.0 ms

GENERALIZED MEASURE OF IMAGE QUALITY IN MEDICAL X-RAY IMAGING

BACKGROUND OF THE INVENTION

1. Field of the Invention

The present invention relates generally to medical X-ray imaging and in particular to a method for determining spatial resolution and noise level in medical projection X-ray imaging.

2. Description of the Related Art

Projection X-ray imaging is used in a medical setting to image structures within the body of a patient. The medical projection X-ray imaging device must be set up to provide a compromise between spatial resolution and noise level. For example, a large focal spot size guarantees a high quantum flux and thus a reduced noise level. On the other hand, image resolutions suffers from a poorly conditioned source. Duration of the exposure also determines image quality since motion of an object during the exposure results in blurring of the object image if the exposure time is too long. On the other hand, short pulses or exposure times reduce the motion blurring effect but lead to high noise levels.

Issues of spatial resolution, contrast, and noise are addressed by the following methods.

In CNR (contrast to noise ratio) or SDNR (signal difference to noise ratio) techniques, the two noted parameters combine contrast and noise.

In MTF (modulation transfer function) techniques, the function describes the loss of modulation amplitude for every spatial frequency, which is caused by the imaging system.

In DQE (detective quantum efficiency) techniques, the function describes the detected performance of a detector compared to an ideal detector, which is in reference to spatial resolution, contrast and noise.

In NPS (noise power spectrum) techniques, the frequency-dependent noise level is considered.

The exposure parameters on an X-ray system are usually chosen in such a way as to ensure a constant detector dose by an automatic exposure control system (AEC). The properties of the object being imaged, such as the speed of an object in motion, are not taken into account.

SUMMARY OF THE INVENTION

The present invention provides a method for determining exposure parameters in an X-ray imaging device.

The objective quality of medical X-ray images is basically determined by three parameters: spatial resolution, contrast and noise. These three parameters are integrated into a single function according to the present invention, the function being the frequency-dependent signal-to-noise ratio SNR=SNR (u,v). This function describes the ratio between the signal and the noise detected in the X-ray image which is dependent on the two-dimensional spatial frequencies u and v.

Let H(u,v) be the Fourier transform of the deterministic signal h(x,y) and NPS(u,v) be the corresponding noise power spectrum, the frequency-dependent signal-to-noise ratio SNR(u,v) can be calculated by:

$$SNR(u, v) = \frac{|H(u, v)|}{\sqrt{NPS(u, v)}} \quad (1)$$

As a fundamental aspect of the present invention, a set of exposure parameters are determined in such a way that the value of SNR(u,v) will achieve its maximum value.

In particular, the equation SNR(u,v) includes spatial resolution and noise information. The contrast in the image, in terms of the signal difference, is incorporated into the spatial-frequency-dependent signal. A high contrast image results in a strong signal amplitude in the corresponding frequency band. A linearity between the contrast (the signal difference) and the value of SNR(u,v) is a consequence of the following mathematical relations:

signal $\Leftrightarrow$ modulus of the Fourier transform $h(x,y) \Leftrightarrow |H(u,v)|$ $a \cdot h(x,y) + b \Leftrightarrow |a \cdot H(u,v) + b \cdot \delta(u) \cdot \delta(v)|. \quad (2)$ For u or v unequal to zero, the modulus of H(u,v) is proportional to any signal scaling.

The value of SNR(u,v) is invariant to linear deterministic image-processing algorithms. Neither a variation of image brightness or contrast, nor the application of spectral filters (high-pass filter, low-pass filter, harmonization, etc.) have any influence on the frequency-dependent value SNR(u,v).

BRIEF DESCRIPTION OF THE DRAWINGS

FIG. 1a is a side view of a geometrical model and FIG. 1b is a top view of the geometrical model used for the calculation of the formula according to the present invention;

FIG. 2 is a flow chart illustrating the calculation procedure for the present method;

DETAILED DESCRIPTION OF THE PREFERRED EMBODIMENTS

Figure 3:
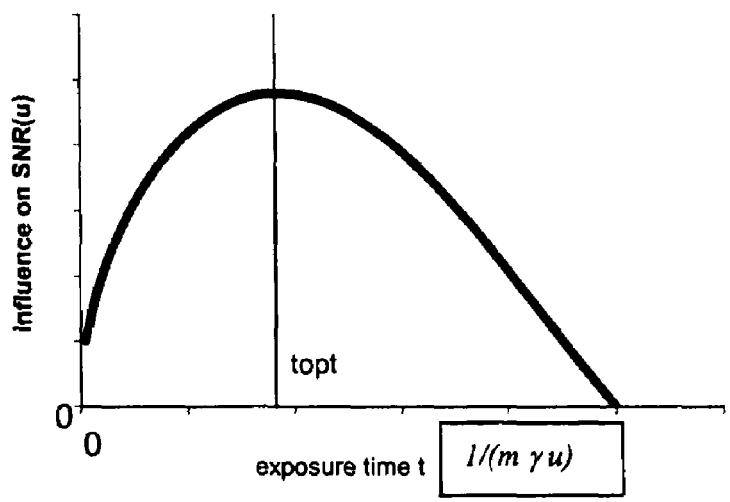
FIG. 3 is a graph showing an influence of exposure time on the present method for a given spatial frequency, velocity of object and magnification factor.

A method for optimizing a medical projection X-ray imaging device provides a single function, namely the frequency-dependent signal-to-noise ratio SNR which incorporates spatial resolution, contrast and noise. The frequency-dependent signal-to-noise ratio SNR describes the ratio between the signal and noise detected in the X-ray image dependent on two-dimensional spatial frequencies u and v so that SNR=SNR(u,v).

The calculation of SNR(u,v) utilizes the Fourier transform of the deterministic signal h(x,y) as the value H(u,v) and the noise power spectrum signal NPS(u,v) according to the following formula:

$$SNR(u, v) = \frac{|H(u, v)|}{\sqrt{NPS(u, v)}} \quad (1)$$

The noise power spectrum is only defined if the underlying signal is spatially invariant. An object of interest which is being imaged by the X-ray, however, absorbs either more or less radiation than the background. As such, the noise power spectrum is different at the location of the object of interest. Assuming that the object of interest is small and that the signal difference between the object signal and the signal of the background is also small, the noise power spectrum can be determined at a position of a sufficiently large, homogeneous background area.

The formula for the frequency-dependent signal-to-noise ratio SNR(u,v) includes spatial resolution information and noise information. The contrast in the image signal in terms of the signal difference is incorporated in the spatial frequency-dependent signal. A high contrast image results in a strong signal amplitude in the corresponding frequency band. The linearity between the contrast (or signal difference) and the formula SNR(u,v) is a consequence of the following mathematical relations:

signal⇔ modulus of the Fourier transform h(x,y)⇔ |H(u,v)| a·h(x,y)+b⇔ |a·H(u,v)+b·δ(u)·δ(v)|. (2)

For values of u or v which are not equal to zero, the modulus of H(u,v) is proportional to any signal scaling.

The formula SNR(u,v) is invariant to linear deterministic image-processing algorithms. Neither a variation of image brightness or contrast, nor the application of spectral filters (such as a high pass filter, low pass filter, harmonization, etc.) have any influence on the frequency-dependent formula SNR(u,v).

The formula for the frequency-dependent signal-to-noise ratio is related to the detective quantum efficiency DQE(u, v). The detective quantum efficiency DQE(u,v) describes the performance properties of a detector, while the signal-to-noise ratio SNR(u,v) is focused on the complete X-ray imaging system and setup, measuring its ability to detect a certain object. This can be expressed mathematically wherein SNR(u,v) is the signal-to-noise ratio at the output of the detector while the detective quantum efficiency DQE(u, v) is the ratio between the squared SNR(u,v) values at the output and at the input of the detector, as follows:

$$DQE(u, v) = \frac{SNR_{out}^2(u, v)}{SNR_{in}^2(u, v)} \quad (3)$$

The signal-to-noise ratio (u,v) like the detective quantum efficiency DQE(u,v) is not a single number but a function. Here, the spatial frequencies u and v that are used in the function SNR(u,v) refer to the detector plane. To be able to use this parameter in a real scoring system for an X-ray system and setup, it must be determined which spatial resolution, in other words which spatial frequency region, is most important for the actual detection problem. If thin guide wires have to be observed, the function SNR(u,v) should be analyzed for higher spatial frequencies. Images of soft tissue, on the other hand, require large SNR(u,v) values in the low frequency domain. Furthermore, when imaging an object, it is important to know whether the object itself or whether the details of that object are to be imaged. For example, it may be desired to image a possible stenosis in the vascular system.

Parameters involved in the formulation of SNR(u,v) using a pulsed source X-ray imaging system include: the object (whether the object to be imaged are guide wires, stents, contrast-media-filled vessels with iodine or $CO_2$, etc.), the source-to-image distance (SID), the geometrical magnification factor of the object, the size of the detector, the patient thickness, the tube voltage U, the material and thickness of the pre-filter, the tube current I, and the exposure time t.

Of the foregoing important parameters, the first five, namely the object, source to image distance, geometrical magnification factor of the object, size of the detector, and patient thickness, are more or less defined by the attending physicist using the task parameters. The last four variables, namely the tube voltage, pre-filter material and thickness, tube current, and exposure time, can either be selected manually or chosen by an automatic exposure control of the X-ray imaging device. These are referred to as optimization parameters.

Turning now to FIGS. 1a and 1b, a geometrical model is utilized for the calculation of the function SNR(u,v). In the model, a tube focus 10 emits an X-ray signal toward a pre-filter 12 so that the X-ray passes through a background 14 in an effort to image an object 16 imbedded in the background 14. X-ray signals which have passed through the background 14 and object 16 are captured by an anti-scattering grid 18 and detected by an active detective layer 20.

In the geometrical model, the background 14 is represented by a cube that is of pure water, Lucite, or a mixture of soft tissue and bones. These are materials which have absorption properties that are close to those of the human body. The thickness of the cube defines the patient thickness. An appropriate simplified shape for the objects of interest 16 such as guide wires or vessels is provided as a cylinder whose axis is perpendicular to the beam direction. The object of interest 16 is situated in the center of the cube 14 representing the background.

The calculation procedures will now be described. Because of the limited calculation power of present-day computers, it is not possible to simulate a complete X-ray image by a pure Monte Carlo track structure calculation technique for the determination of the function SNR(u,v). The problem is solved by a combination of three different strategies. First, deterministic calculations are performed, second, stochastic simulations (which are equivalent to a Monte Carlo track structure) are performed, and thirdly, analytical calculations (a cascaded model) are performed. The whole process of the calculation of the function SNR (u,v) is illustrated in FIG. 2, wherein deterministic calculations 22 are performed to provide a sharp noiseless image 24. A blurring function 26 is performed to generate a blurred noiseless image 28 which is then provided to a Fourier transform of the absolute, blurred noiseless image 30 that is then provided to the signal-to-noise ratio SNR(u,v) 32. Further stochastic simulations 34 are performed to generate absorption probability, the ratio of scatter-to-primary edge deposition, the mean energy deposition per quantum, and the variance of the absorbed x ray spectrum 36. This results in an absolute signal of the background NPS(u, v) 38 which is then provided to both the Fourier transform 30 and the signal-to-noise ratio 32. Further, analytical calculations 40 are provided as a cascaded model. The output of the calculations is the absolute signal of the background when combined with the information 36 which are then provided to the Fourier transform 30 and the signal-to-noise ratio 32.

In particular, deterministic calculations are provided as follows: A pencil-shaped X-ray beam from the focal spot to the center of the detector pixel is considered for every detector pixel. With the information on the material composition, the density, and the thickness of the beam, it is possible to calculate the average probability of primary X-ray quanta with an energy spectrum defined by the tube setup (including the anode material, the anode angle, and the tube voltage) being registered in the active layer of the detector. The absolute signal height cannot be determined by the deterministic calculations since the scatter radiation information is missing. To avoid sampling effects due to a finite pixel size at that stage, the real pixel length is reduced. To summarize, the result of this deterministic calculation 22 is an extremely sharp, noiseless X-ray image 24, given in relative intensities. In a preferred embodiment, the deterministic calculations 22 are performed utilizing a program named DRASIM, which is an internal program of Siemens AG. Primary X-ray spectra can be taken from the publications by Boone et al., "An accurate method for computer generated tungsten anode x-ray spectra from 30 to 140 kV", Med Phy 24, 1661-1670, 1997 and Aichinger et al., "Radiation Exposure and Image Quality in X-ray Diagnostic Radiology", Springer-Verlag, Berlin 2004

Subsequently, the perfect images are analytically blurred, at 26. The blurring is done in the frequency domain. The images 28 are Fourier transformed at 30 and scaled with the corresponding MTF(u,v) functions where (u,v) are the spatial frequencies in the x and y directions, respectively. For the determination of the MTF(u,v) function, the following Fourier transform of a rectangular input function with a base length a is helpful.

$$FT\left\{rect\left(\frac{x}{a}\right)\right\} = FT\left\{\begin{matrix} 1, & |x| < \frac{a}{2} \\ 0, & |x| \geq \frac{a}{2} \end{matrix}\right\} = a \cdot \text{sinc}(a \ f) = a \cdot \frac{\sin(\pi a f)}{\pi a f} \quad (4)$$

Four blurring sources are considered: the focal spot, motion blurring, the scattering of quanta in the detector, and detector pre-sampling.

Let $f_x$ and $f_y$ be the sizes of a rectangular focal spot and $\gamma$ the magnification factor of the object of interest ($\gamma=1 \Rightarrow$ object is directly on the surface of the detector; $\gamma=2 \Rightarrow$ object is exactly half way between focal spot and the detector) such that the corresponding MTF is:

$$\text{MTF}_{foc}(u,v) = \text{sinc}(f_x(\gamma-1)u) \ \text{sinc}(f_y(\gamma-1)v) \quad (5)$$

Let $m_x$ and $m_y$ be the velocity of the object of interest rectangular to the X-ray beam direction, t the exposure time, and $\gamma$ the above defined magnification factor such that the corresponding MTF is:

$$\text{MTF}_{mot}(u,v) = \text{sinc}(m_x t \gamma u) \text{sinc}(m_y t \gamma v) \quad (6)$$

X-ray quanta and optical quanta in the case of an indirect-detection detector cause blurring. A real corresponding $\text{MTF}_{sci}(u,v)$ function is difficult to calculate due to the lack of a precise description of the optical properties of the scintillator. Instead of doing so, it should be measured. If scattering of X-ray quanta in the active layer and variable interaction depths in the scintillator are neglected, a single MTF function for all quanta with different energies and absorption depths can be defined.

Let $a_x$ and $a_y$ be the sizes of the active regions of a detector pixel such that the corresponding MTF is:

$$\text{MTF}_{pix}(u,v) = \text{sinc}(a_x u) \cdot \text{sinc}(a_y v) \quad (7)$$

In FIG. 2, the stochastic simulations 34 of the preferred embodiment are based on Monte Carlo track structure calculations. The direction and energy and the emitted X-ray quanta are randomly chosen from a given angle and with know energy distributions. The complete history of the primary particles and all possible secondary particles is tracked. For example, all photon interactions with the pre-filter, the background object, the anti-scatter grid, and finally the active layer of the detector are simulated to determine the energy deposition distribution. These photon interactions include the photoelectric effect, coherent scattering, incoherent scattering, and K fluorescence. The object of interest can be omitted in these simulations since its total influence is assumed to be negligibly small. The statistics, obtained by tracking approximately $10^8$ quantum histories, are good enough to find out the following system properties, assuming the scatter radiation is homogeneously distributed over the whole detector area: the number of absorbed quanta N (including the primary and secondary quanta) in the active layer of the detector per emitted primary quantum, ratio S/P between the secondary energy deposition and the primary energy deposition in the active layer of the detector, mean deposited energy <E> per absorbed quantum, and the variance of energy $\sigma_E^2$ of absorbed quanta. The stochastic simulations 34 are performed, in a preferred embodiment, by a program named MOCASSIM, which is an internal program of Siemens AG.

In FIG. 2, the analytical calculations 40 are provided as a cascaded model. The influence of the physical processes in the flat panel detector on the uniform image (which is the image without an object of interest) can be described with the help of a linear cascaded model. The process is divided into five steps, for example, the conversion of the X-ray quanta to optical quanta in the scintillator, the scattering of optical quanta in the scintillator, the selection of light quanta, the spatial integration of interacting light quanta, and the output of the discrete detector elements.

In every step of the analytical calculations 40, the quantum flux q (which is the mean number of particles per unit area) and the corresponding noise power spectrum NPS(u, v) are updated. The input parameters $q_0$ and $\text{NPS}_0(u,v)$ can be calculated with the help of the number of absorbed quanta N, the SID (source-to-image distance), the X-ray tube gain Q for a certain tube voltage (which is in 1/mAs/sr), the tube current I, and the exposure time t:

$$q_0 = \frac{N \cdot Q \cdot I \cdot t}{(SID)^2} \quad (8)$$

$$NPS_0(u,v) = \frac{N \cdot Q \cdot I \cdot t}{(SID)^2}$$

The conversion of the X-ray quanta into optical quanta can be split into two gain processes: the first process provides that the energy of the quantum is distributed via secondary particles (which are mainly electrons). The second process provides that the optical transitions, caused by the electrons in the scintillator, generate optical quanta.

The energy deposition has a gain factor which is equivalent to the mean deposited energy <E> per primary X-ray quantum, and the variance $\sigma_E^2$ of this process is dependent on the width of the absorbed spectrum. Both values are determined during the statistical simulations.

A mean gain factor <G> for the generation of optical quanta is dependent on the scintillator material; the gain factor is given in optical quanta per absorbed energy. In the case of CsI, the mean gain factor <G> is approximately 55/keV[10]. Under the assumption of Poisson statistics, the variance of this distribution is $\sigma_G^2 = <G>$.

It is important to note that both of these gain processes always have to be combined. The energy deposition is not a real gain process, since energy units and particles are not produced. It is only justified by immediate application of a second gain process. The resulting quantum flux $q_1$ and $NPS_1$ are $$q_1 = <E><G>q_0 \text{NPS}_1(u,v) = <E>^2<G>^2 \text{NPS}_0(u,v) + <G>^2\sigma_E^2 q_0 + \sigma_G^2 <E> q_0 \quad (9)$$

Assuming a unique $\text{MTF}_{sci}(u,v)$ for all optical quanta inside the scintillator, the resulting quantum flux $q_3$ and $NPS_3$ are:

$$q_2 = q_1 \text{NPS}_2(u,v) = (\text{NPS}_1(u,v) - q_1) \cdot \text{MTF}_{sci}^2(u,v) + q_1 \quad (10)$$

The probability β for the detection of the optical quanta includes the coupling efficiency of light from the scintillator as well as the quantum efficiency of the detector array. This gain process results in the following flux q3 and $NPS_3$:

$$q_3 = \beta q_2 \text{NPS}_3(u,v) = \beta^2(\text{NPS}_2(u,v) - q_2) + \beta q_2 \quad (11)$$

The detector pre-sampling signal corresponds to the spatial integral over the active region of a detector pixel with a width of $a_x$ and $a_y$, respectively. The new flux $q_4$ and the $NPS_4$ equals:

$$q_4 a_x a_y q_3 \text{NPS}_4(u,v) = a_x^2 a_y^2 \text{NPS}_3(u,v) \cdot \sin c^2(a_x u) \cdot \sin c^2(a_y v) \quad (12)$$

Finally, the discrete detector signal is recorded. Let $x_0$ and $y_0$, respectively, be the distances between the center of two neighboring pixels such that the expected digital signal value $q_5$ of a pixel and the digital $NPS_5$ are:

$$q_5 = q_4 \quad (13)$$

$$NPS_5(u,v) = NPS_4(u,v) + \sum_{n_x=1}^{\infty} \sum_{n_y=1}^{\infty} NPS_4\left(u \pm \frac{n_x}{x_0}, v \pm \frac{n_y}{y_0}\right)$$

The final calculation of the function SNR(u,v), at element 32 in FIG. 2, is performed with the help of the scatter-to-primary ratio S/P and $q_5$, the intensities of the noiseless, blurred image can be scaled. Assuming that the object of interest is small and that the scatter radiation is homogeneously distributed over the whole image area, a constant amount of scatter, which is the product of the actual background intensity and the S/P, is added to all pixels of the image. Then the image is scaled to achieve a background intensity of $q_5$, where the artificially reduced pixel length of the deterministic calculation 22 has to be considered. The Fourier transform H(u,v) can now be determined from the resulting scaled image. Finally, the function SNR(u,v) can be calculated according to the following:

$$SNR(u,v) = \frac{|H(u,v)|}{\sqrt{NPS_5(u,v)}} \quad (14)$$

For every point in the exposure parameter space, the function SNR(u,v) can thus be obtained. The results can be used to find the optimum parameter setup for the X-ray imaging device.

Electronic noise, which is independent of detector dose, has been neglected in this derivation, which is justified only for sufficiently high detector doses. Nevertheless, the method can easily be extended to include these effects.

The following describes motion blurring verses high dose imaging. An advantage of the image quality parameter SNR(u,v) defined here is the ability to find the best compromise between image sharpness and noise. In the following example, the optimum exposure time is determined for the detection of moving guide wires, which are typically used in cardiology. In the following example, the guide wires have a substantially cylindrical shape have, a diameter of d, and we moved at a velocity m which is perpendicular to the axis of the wire, and the system has a magnification factor of γ. The tube voltage and the tube current are fixed in this example.

Since a constant motion can be fully described in one dimension, it is sufficient here to determine the influence of the exposure time t on the one-dimensional function SNR(u). Here, u is the corresponding spatial frequency with respect to the direction of motion. The exposure time t affects the function SNR(u) in two ways: First, a long exposure time generates blurring of the image because the object is moving. For a constant tube current during the X-ray pulse, the influence on SNR(u) can be described by:

$$SNR(u) \propto \sin c(mu\gamma t) \quad (15)$$

Secondly, increasing exposure times raise the contrast and noise levels. See equation (8). In total, according to equation (14), the formula SNR(u) behaves like:

$$SNR(u) \propto t \cdot \frac{1}{\sqrt{t}} = \sqrt{t} \quad (16)$$

Equations 15 and 16 can be combined to yield the following:

$$SNR(u) \propto \frac{\sin(\pi mu\gamma t)}{\pi mu\gamma \sqrt{t}} \quad (17)$$

Referring now to FIG. 3, one can think of an optimal exposure time for the X-ray image. The dependence of the formulation SNR(u) on exposure time t is given in the figure wherein a fixed spatial frequency u, a velocity m of the object, and a magnification factor γ are provided.

With increasing exposure time, the number of quanta arises. The object dominates more and more over the background noise. A further increase in the exposure time leads to enhanced motion blurring, and a deterioration the image quality. Thus, there is an optimal value $t_{opt}$ for the exposure time, which is given by:

$$t_{opt} \approx \frac{0.37}{m\gamma u} \quad (18)$$

The foregoing formula is a result of an analysis of a transcendental equation, which leads to the coefficient of 0.37. This result for the option time $t_{opt}$ shall be illustrated.

A spatial frequency or the center frequency band has to be found, which is, for example, the importance for the detection of a guide wire. The frequency, whose half wave length is equal to the size $\gamma d$ of the guide wire in the detector plane is presumed to be a major contributing. Hence, the formula $$u = \frac{1}{2d\gamma},$$

which enables the Equation (18) to be rewritten as:

$$t_{opt} \approx \frac{0.74d}{m} \quad (19)$$

In the foregoing formula, d/m is the time period which is necessary for one edge of the guide wire to pass the original position of the other edge. Here, an adequate exposure time for imaging moving guide wires is given when there is an overlap of approximately 25% between the guide wire at the beginning and at the end of the exposure, which is independent of the magnification factor.

Figure 4:
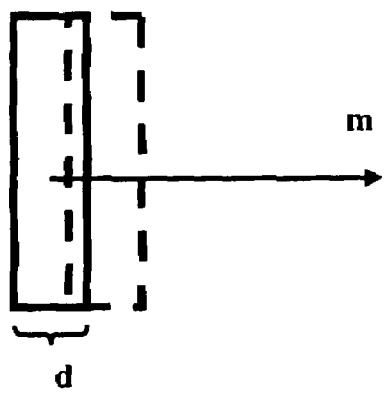
FIG. 4 is a schematic representation of an optimum exposure time for a guide wire moving perpendicular to its axis.
Figure 5:
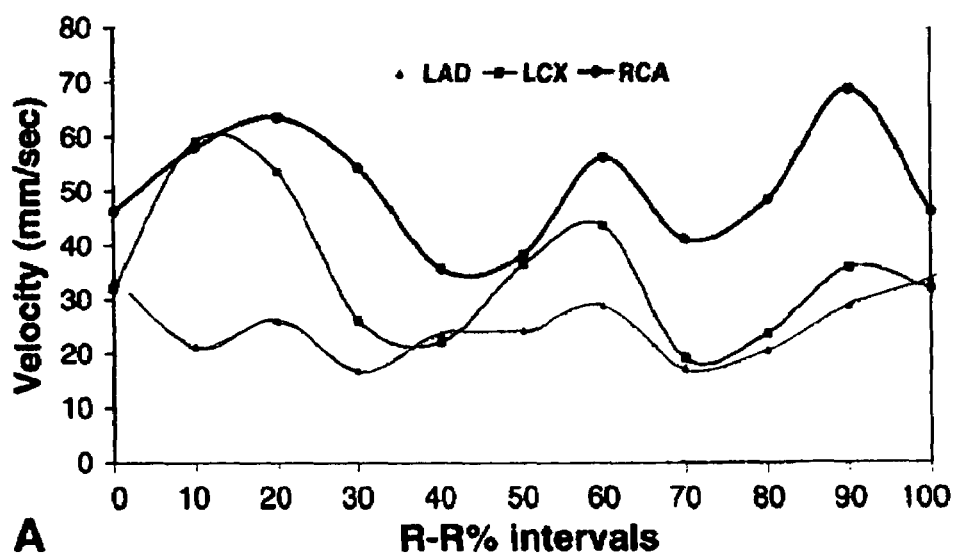
FIG. 5 is a graph illustrating velocities of a cardiac cycle for different regions of a heart at 72 beats per minute.
Figure 6A:
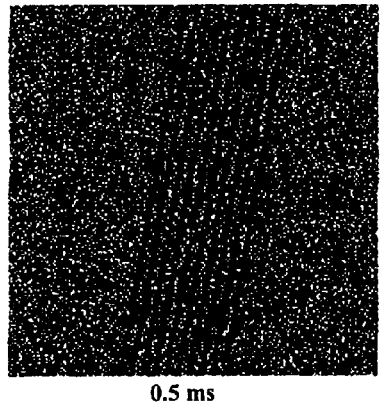
FIGS. 6a, 6b, 6c, 6d, 6e and 6f are images of a moving guide wire obtained with different exposure times.
Figure 6B:
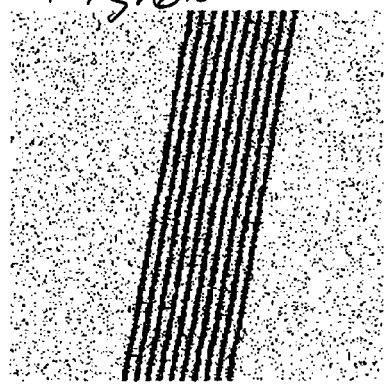
Figure 6C:
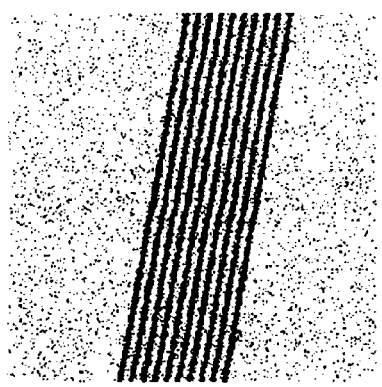
Figure 6D:
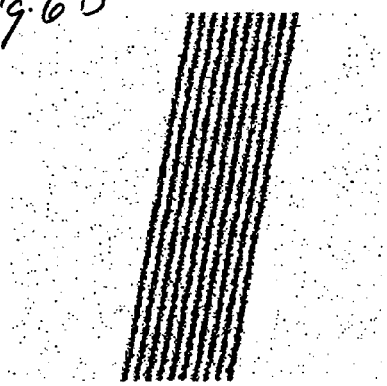
Figure 6E:
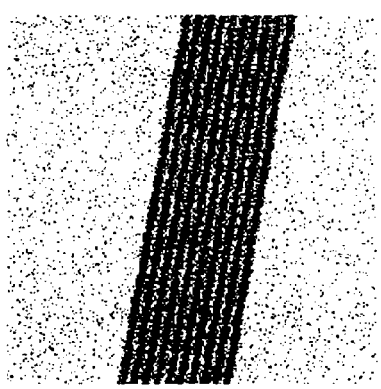
Figure 6F:
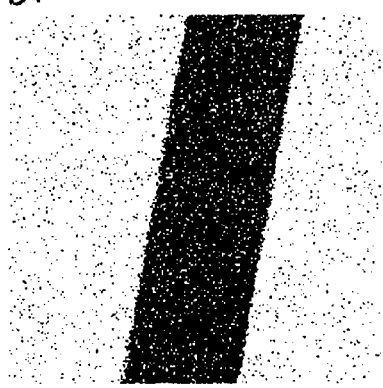

Turning now to FIG. 4, an illustration of the optimum exposure time for a guide wire moving perpendicular to its axis is provided. The solid line represents the position of the guide wire at the beginning of an exposure and the broken outline gives the position of the guide wire at the end of the exposure. Assuming a typical diameter d of 0.36 mm for a guide wire and a typical average velocity m of 40 mm/s (see FIG. 5) in a cardiology application, the optimum exposure time is approximately 6.7 ms, which is in good agreement with published measurements. In particular, FIG. 5 is a graph illustrating the velocity of a cardiac cycle for different regions of the heart at 72 beats per minute. The designation LAD refers to the left anterior descending coronary artery, LCX refers to the left circumflex, and RCA to the right coronary artery. The velocity in millimeters per second is provided on the vertical axis.

Turning now to FIG. 6, examples of exposures at different times have been simulated example is simulated with the help of the DRASIM program. The exposure time is varied from 0.5 ms to 18 ms. The object in the simulation is a set of parallel orientated guide wires, moving perpendicular to their axis. The detectability increases up to 6.3 ms, whereas motion blurring effects dominate beyond that. Finally, at an exposure of 18 ms, individual guide wires are no more visible.

The use of a set of guide wires instead of a single guide wire has prompted by the fact, that this periodical object is mainly based on the spatial frequency around $$u = \frac{1}{2d\gamma},$$

whereas a single guide wire also includes low-frequency components. These components would profit from long exposure times. Consequently, the detectability of a single guide wire could rise even with increasing exposure time, even if the guide wire becomes more and more blurred. A real anatomical image, however, includes anatomical noise and structures, typically with a high amplitude at lower spatial frequencies, as shown. See FIG. 7 in this regard.

Therefore, it is recommended to focus the optimization on the intrinsic spatial frequencies for a guide wire around $$u = \frac{1}{2d\gamma}.$$

Figure 7:
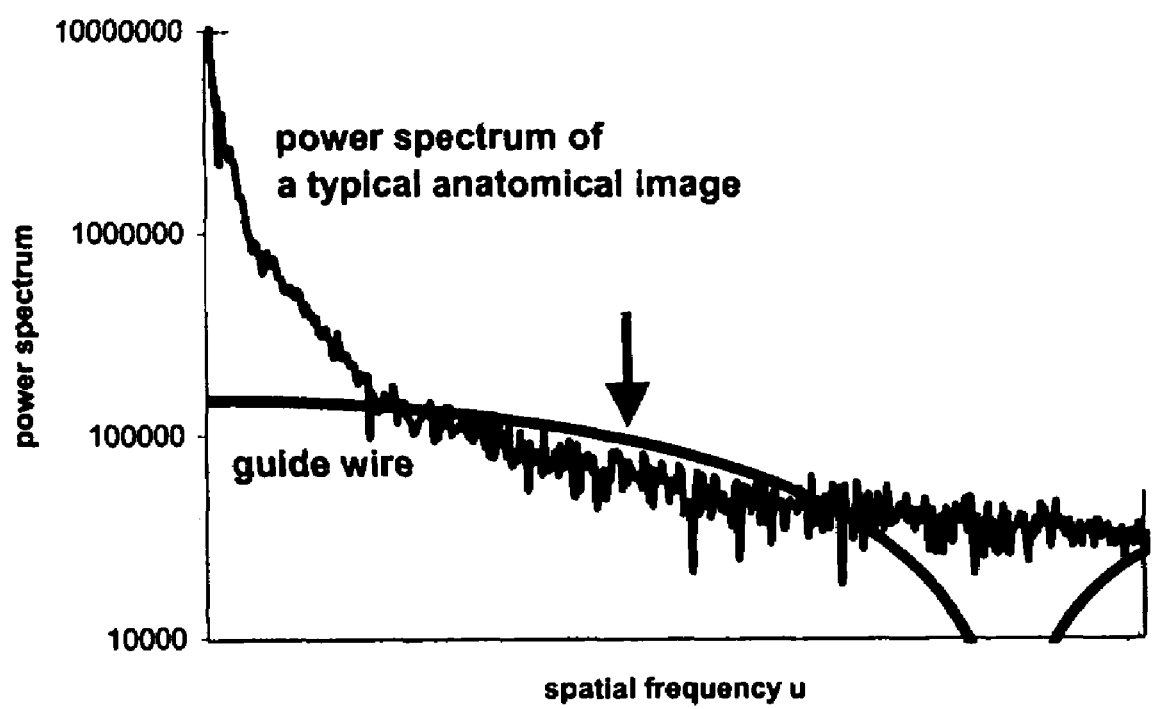
FIG. 7 is a graph of power spectra of a typical anatomical image and a single guide wire.

Referring to FIG. 7, a power spectra for a typical anatomical image and a single guide wire are provided. An arrow has been indicated in the graph to indicate the spatial frequency $$u = \frac{1}{2d\gamma}.$$

Thus, a generalized objective image quality measure has been made for X-ray based medical projection imaging. The spatial frequency-dependent signal-to-noise ratio SNR=SNR(u,v) is disclosed. This function has its origins in the DQE concept. It combines three main objective image quality parameters, namely the spatial resolution, object contrast, and noise. Besides the analytical definition, the present function can be calculated for a test phantom at a typical flat-panel detector by applying a combination of analytical calculations and Monte Carlo simulations. In the example, the function SNR(u,v) is used to optimize a pulsed X-ray imaging device. For a moving object, the most suitable exposure time has been determined.

Thus, there is disclosed a method for providing a generalized objective image quality measurement for an X-ray based medical projection imaging apparatus. The spatial frequency-dependent signal-to-noise ratio function is provided, which includes three main image quality parameters, namely spatial resolution, object contract, and noise. The DQE concept does not characterize the detector, but rather the detectability of certain objects embedded in a defined background. The effects of focus size and radiation scatter are quantified by the present method. The signal-to-noise ratio is independent of basic linear post-processing steps such as appropriate windowing or spatial filtering.

By means of the signal-to-noise ratio, different X-ray systems and setups can be compared with each other and with theoretical calculations. X-ray systems, including the detector, beam quality, geometry, anti-scatter grid, and basic linear post-processing steps etc. can be optimized to deliver the best object detectability for a given patient dose. The signal-to-noise ratio is defined using analytical formulas. The foregoing demonstrates how the function can be applied with a test phantom to a typical flat panel detector system by a combination of analytical calculations and Monte Carlo simulations. The foregoing demonstrates how the signal-to-noise ratio function is used to optimize an X-ray imaging device.

Although other modifications and changes may be suggested by those skilled in the art, it is the intention of the inventors to embody within the patent warranted hereon all changes and modifications as reasonably and properly come within the scope of their contribution to the art.

What is claimed is:

1. A method for quantifying image quality of an x-ray based medical projection imaging system, comprising the steps of:

directing a beam of x-ray energy to a detector to produce an image;

performing a deterministic calculation to determine an average probability for x-ray quanta being absorbed by an active layer of the detector;

blurring the image in a frequency domain to produce a blurred image;

performing a Fourier transform of the blurred image to produce a transformed blurred image;

performing a stochastic simulation based on Monte Carlo track structure calculations for emitted x-ray quanta to determine energy deposition distribution during imaging;

performing an analytical calculation as a linear cascaded model to determine influence of physical processes in the detector;

calculating the spatial frequency dependent signal to noise ratio using output of said Fourier transform and said stochastic simulation and said analytical calculation according to the following:

$$SNR(u, v) = \frac{|H(v, v)|}{\sqrt{NPS_S(u, v)}}; \text{ and}$$

using a result of said calculating step to optimize an X-ray imaging system.

2. A method as claimed in claim 1, wherein said step of performing said Fourier transform includes a step of: scaling the blurred image.

3. A method as claimed in claim 1, wherein said step of performing said stochastic simulation includes:
determining absorption probability;
determining a ratio of scatter to primary energy deposition;
determining a mean energy deposition per quantum; and
determining a variance of absorbed x-ray spectrum.

4. A method as claimed in claim 1, wherein said steps of performing said stochastic simulation and said step of performing said analytical calculation provides a determination of an absolute signal of a background of the image.

5. A method as claimed in claim 1, wherein said step of performing said analytical calculation includes:
converting x-ray quanta to optical quanta;
scattering optical quanta in a scintillator;
selecting light quanta;
spatially integrating interacting light quanta; and
outputting discrete detector elements.

6. A method as claimed in claim 5, wherein said step of converting x-ray quanta to optical quanta includes:
distributing energy of the x-ray quanta via secondary particles; and
generating optical quanta by optical transitions of the secondary particles in a scintillator.

7. A method for optimizing image quality during setup of a medical projection x-ray device, comprising the steps of:
directing a beam of x-ray energy to a detector to produce an image;
performing a deterministic calculation to determine an average probability for x-ray quanta as registered in the detector;
blurring the image in a frequency domain to produce a blurred image;

performing a Fourier transform of the blurred image to produce a transformed blurred image;

performing a stochastic simulation for emitted x-ray quanta to determine energy deposition distribution during imaging;

performing an analytical calculation to determine influence of physical processes in the detector;

calculating the spatial frequency dependent signal to noise ratio using output of said Fourier transform and said stochastic simulation and said analytical calculation according to the following function:

$$SNR(u, v) = \frac{|H(v, v)|}{\sqrt{NPS_S(u, v)}}; \text{ and}$$

adjusting the medical projection x-ray device to maximize a value of SNR(u, v) at a given frequency pair u, v.

8. A method as claimed in claim 7, further comprising the step of:
varying spatial frequency depending on characteristics of an object to be detected to optimize object detection in an image by the x-ray imaging system.

9. A method as claimed in claim 8, wherein said object characteristics include object size and object movement rate.

10. A method for quantifying image quality of an x-ray based medical projection imaging system,
directing a beam of x-ray energy to a detector to produce an image;
performing a deterministic calculation to determine an average probability for x-ray quanta registered in the detector;
blurring the image in a frequency domain to produce a blurred image;
performing a Fourier transform of the blurred image to produce a transformed blurred image;
performing a stochastic simulation for emitted x-ray quanta to determine energy deposition distribution during imaging;
performing an analytical calculation to determine influence of physical processes in the detector;
calculating the spatial frequency dependent signal to noise ratio using output of said Fourier transform and said stochastic simulation and said analytical calculation according to the following function:

$$SNR(u, v) = \frac{|H(v, v)|}{\sqrt{NPS_S(u, v)}}; \text{ and}$$

using a result of said calculating step to optimize an X-ray imaging system.

11. A method as claimed in claim 10, further comprising the step of:
comparing a value produced by said function for said imaging system to a value of said function of another x-ray imaging system.

* * * * *